(12) United States Patent
Tanaka

(10) Patent No.: US 8,968,712 B2
(45) Date of Patent: Mar. 3, 2015

(54) COSMETIC COMPOSITIONS

(75) Inventor: Shuhei Tanaka, Kobe (JP)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 13/300,035

(22) Filed: Nov. 18, 2011

(65) Prior Publication Data
US 2012/0128603 A1 May 24, 2012

Related U.S. Application Data

(60) Provisional application No. 61/415,019, filed on Nov. 18, 2010.

(51) Int. Cl.
A61K 8/00 (2006.01)
A61K 8/02 (2006.01)
A61K 8/34 (2006.01)
A61K 8/44 (2006.01)
A61Q 19/00 (2006.01)
A61Q 5/00 (2006.01)
A61Q 19/08 (2006.01)
A61Q 3/00 (2006.01)
A61Q 17/04 (2006.01)
A61Q 19/02 (2006.01)

(52) U.S. Cl.
CPC . A61K 8/44 (2013.01); A61Q 5/002 (2013.01); A61K 8/342 (2013.01); A61Q 19/08 (2013.01); A61Q 3/00 (2013.01); A61Q 17/04 (2013.01); A61K 2800/10 (2013.01); A61Q 19/02 (2013.01); A61Q 19/00 (2013.01)
USPC .............................. 424/62; 424/63; 424/401

(58) Field of Classification Search
None
See application file for complete search history.

(56) References Cited

U.S. PATENT DOCUMENTS

| 3,755,560 | A | | 8/1973 | Dickert et al. |
| 4,421,769 | A | | 12/1983 | Dixon et al. |
| 4,970,252 | A | | 11/1990 | Sakuta et al. |
| 5,254,338 | A | * | 10/1993 | Sakai et al. ................. 424/78.35 |
| 5,654,362 | A | | 8/1997 | Schulz, Jr. et al. |
| D391,162 | S | | 2/1998 | Kokenge |
| 5,760,116 | A | | 6/1998 | Kilgour et al. |
| 5,958,386 | A | * | 9/1999 | Sawin et al. ..................... 424/65 |
| 6,174,533 | B1 | | 1/2001 | Sanogueira |
| 6,790,435 | B1 | * | 9/2004 | Ma et al. ......................... 424/65 |
| 6,939,537 | B2 | | 9/2005 | Ohta et al. |
| D516,436 | S | | 3/2006 | Campbell et al. |
| 7,054,674 | B2 | | 5/2006 | Cane et al. |
| D535,191 | S | | 1/2007 | Corker |
| D542,660 | S | | 5/2007 | Thomas et al. |
| D547,193 | S | | 7/2007 | Blasko et al. |
| D547,661 | S | | 7/2007 | Blasko et al. |
| D558,591 | S | | 1/2008 | Blasko et al. |
| D563,221 | S | | 3/2008 | Ashiwa et al. |
| 7,347,990 | B2 | | 3/2008 | Emslie et al. |
| D570,707 | S | | 6/2008 | Blasko et al. |
| 2004/0142853 | A1 | | 7/2004 | Patt |
| 2004/0175347 | A1 | | 9/2004 | Bissett |
| 2005/0019356 | A1 | | 1/2005 | Bissett |
| 2005/0118119 | A1 | | 6/2005 | Stoltz |
| 2006/0089553 | A1 | | 4/2006 | Cotton |
| 2006/0275237 | A1 | | 12/2006 | Bissett |
| 2007/0040306 | A1 | | 2/2007 | Morel et al. |
| 2007/0203240 | A1 | | 8/2007 | Oblong et al. |
| 2007/0205226 | A1 | | 9/2007 | Honda et al. |
| 2007/0292358 | A1 | * | 12/2007 | Emmerling et al. ............ 424/47 |
| 2007/0297996 | A1 | * | 12/2007 | Tanner ............................. 424/59 |
| 2008/0057015 | A1 | | 3/2008 | Oblong et al. |
| 2008/0059313 | A1 | | 3/2008 | Oblong et al. |
| 2008/0206373 | A1 | * | 8/2008 | Millikin et al. ................ 424/769 |
| 2008/0241088 | A1 | * | 10/2008 | Joshi et al. ....................... 424/65 |
| 2008/0305059 | A1 | * | 12/2008 | Chaudhuri ...................... 424/62 |
| 2009/0017080 | A1 | | 1/2009 | Tanner et al. |
| 2009/0317345 | A1 | * | 12/2009 | Joshi et al. ....................... 424/65 |
| 2010/0183527 | A1 | | 7/2010 | Moser et al. |
| 2010/0186669 | A1 | | 7/2010 | Shin et al. |
| 2012/0148510 | A1 | | 6/2012 | Hakozaki |
| 2012/0148515 | A1 | | 6/2012 | Hakozaki |
| 2012/0156146 | A1 | | 6/2012 | Hakozaki |

FOREIGN PATENT DOCUMENTS

| DE | 19928112 | 12/2000 |
| EP | 1325737 | 7/2003 |
| EP | 1790330 A2 | 5/2007 |
| EP | 1810614 A2 | 7/2007 |
| EP | 1980237 A1 | 10/2008 |
| EP | 2014276 A1 | 1/2009 |
| FR | 2913598 | 9/2008 |
| JP | 6118708 A | 4/1994 |
| JP | 2006016401 | 1/2006 |
| WO | 2010110863 A2 | 9/2010 |

OTHER PUBLICATIONS

Mintel Database "Youth Body Cream", Guinot, Jun. 2010, 5 pages http://www.gnpd.com.
Mintel Database Jan. 2010 "Neck and Decollete Care" 4 pages http://www.gnpd.com.
Mintel Database Jun. 2009. "Moisturize Anti-Wrinkle Skin Firming Hydrator" April Rain Skin Science, 8 pages http://www.gnpd.com.
Mintel Database Apr. 2011. "Enriched Body Care" Mary Cohr. 5 pages http://www.gnpd.com.
Mintel Database "High Performance Hair Growth Stimulating Conditioner", DS Laboratories Feb. 2011, 5 pages http://www.gnpd.com.
Matts, P., New Insights Into Skin Appearance and Measurement, Journal of Investigative Dermatology Symposium Proceedings (2008), 13, 6-9.

(Continued)

Primary Examiner — Susan Tran
(74) Attorney, Agent, or Firm — John G. Powell

(57) ABSTRACT

A cosmetic composition comprises a) an N-acyl amino acid compound selected from the group consisting of N-acyl amino acid, its isomers, its salts, derivatives thereof, and mixtures thereof, and b) hexyldecanol.

15 Claims, No Drawings

(56) References Cited

OTHER PUBLICATIONS

International Search Report; PCT Application No. PCT/US2011/061160; mailing date May 24, 2012; 14 pages.
International Search Report; PCT Application No. PCT/US2011/061167; mailing date Jun. 5, 2012; 14 pages.
International Search Report; PCT Application No. PCT/US2011/061159; mailing date May 24, 2012; 15 pages.
USPTO Office Action rejections/objections from co-pending U.S. Appl. No. 13/298,985, filed Nov. 17, 2011, Inventor Tomohiro Hakozaki, et al., Mail Date Nov. 21, 2012, 12 pages.
USPTO Office Action rejections/objections from co-pending U.S. Appl. No. 13/299,042, filed Nov. 17, 2011, Inventor Tomohiro Hakozaki, et al., Mail Date Sep. 26, 2012, 29 pages.
Mintel Database Oct. 2010. "Cellular Total Eye Care" La Colline Cellulary Research Laboratories, 6 pages http://www.gnpd.com.
Mintel Database May 2008."Color Repair Tinted Moisturizing Anti-Wrinkle Cream" Institut Esthederm, 3 pages http://www.gnpd.com.
Mintel Database Oct. 2011."Dark Spot Corrector" Philosophy, 5 pages http://www.gnpd.com.
Mintel Database Feb. 2005."Extreme Bronz Repair Tanning Cream" Mary Cohr, 5 pages http://www.gnpd.com.
Mintel Database Nov. 2011."Serum" Institut Esthederm, 2 pages http://www.gnpd.com.
Mintel Database Oct. 2003."Supertanning Moisturising Mild Spray SPF 15" Collistar, 3 pages http://www.gnpd.com.
Mintel Database Oct. 2003."Virtual Youth Lifting Moisture Makeup (35)" Prescriptives 2 pages http://www.gnpd.com.
Mintel Database Dec. 2009."White Crystal BB Cream SPF 35/PA++" The Face Shop, 3 pages http://www.gnpd.com.
"Use of UV absorbers in combination with skin lightening agents to optimize the preventing tanning", IP.Com Journal, IP.Com Inc., Westhenrietta. NY, US. Jan. 4, 2008; p. 55-p. 56.
"Undecyl-10-enoyl-phenylalanine (Sepiwhite) provides additional benefits to the cosmetic ingredients N-acetyl glucosamine and niacinamide in the regulation of melanin production in vitro". Journal of the American Academy of Dermatology, CV. Mosby. St. Louis, MO, US, vol. 58. No. 2. Feb. 1, 2008 p. AB118.
International Search Report; PCT Application No. PCT/US2011/060904; mailing date Apr. 26, 2012; 17 pages.
Sepiwhite Msh. Research Disclosure. Mason Publications Hampshire. GB. vol. 462, No. 21. Oct. 1, 2002.
Bissett Donald L et al: "Reduction in the appearance of facial hyperpigmentation by topical N-undecyl-10-enoyl-L-phenylalanine and its combination with niacinamide", Journal of Cosmetic Dermatology. Blackwell Science, Oxford. GB, vol. 8, No. 4. Dec. 1, 2009, pp. 260-266.

\* cited by examiner

COSMETIC COMPOSITIONS

CROSS REFERENCE TO RELATED APPLICATION(S)

This application claims the benefit of U.S. Provisional Application No. 61/415,019, filed on Nov. 18, 2010.

FIELD OF THE INVENTION

The present invention relates to cosmetic composition containing an N-acyl amino acid compound, and preparation methods thereof. Such compositions are useful for regulating the condition of mammalian keratinous tissue needing such treatments.

BACKGROUND OF THE INVENTION

Mammalian keratinous tissue, particularly human skin, is subjected to a variety of insults by both extrinsic and intrinsic factors. Such extrinsic factors include ultraviolet radiation, environmental pollution, wind, heat, infrared radiation, low humidity, harsh surfactants, abrasives, etc. Intrinsic factors, on the other hand, include chronological aging and other biochemical changes from within the skin. Whether extrinsic or intrinsic, these factors result in visible signs of skin damage. Typical skin damage in aging or damaged skin include fine lines, wrinkling, hyperpigmentation, sallowness, sagging, dark under-eye circles, puffy eyes, enlarged pores, diminished rate of turnover, and abnormal desquamation or exfoliation. Additional damage incurred as a result of both external and internal factors includes visible dead skin i.e., flaking, scaling, dryness, and roughness.

Currently, there are a number of personal care products that are available to consumers, which are directed toward improving the health and physical appearance of keratinous tissues such as the skin, hair, and nails. The majority of these products are directed to delaying, minimizing or even eliminating skin wrinkling, spots, and other histological changes typically associated with the aging of skin or environmental damage to human skin. Consumers prefer topically applied products since they are not only effective, but also safe and pleasant to use.

An N-acyl amino acid, particularly N-acyl derivatives of phenylalanine or tyrosine, their isomers, or their salts are known for being useful in preventing or treating various keratinization disorders. These compounds are cosmetic active agents of choice such as for whitening products.

However, it has been observed that these compounds are difficult to dissolve in cosmetic compositions, and these active agents have a tendency to recrystallize. Oil compounds such as Eldew SL-205 from Ajinomoto, and octyldodecanol are known as an solvent for N-acyl amino acid compounds.

Based on the foregoing, there is a continuing need to formulate cosmetic compositions containing an N-acyl amino acid compound that can provide stable delivery of skin actives.

SUMMARY OF THE INVENTION

The present invention relates to a cosmetic composition comprising a) an N-acyl amino acid compound selected from the group consisting of N-acyl amino acid, its isomers, its salts, derivatives thereof, and mixtures thereof, and b) hexyldecanol.

The present invention also relates to methods of using such compositions to regulate the condition of skin, said method comprising applying to the skin of a human in need of treatment.

The present invention also relates to a method of preparing a cosmetic composition comprising, dispersing a first oil phase comprising an N-acyl amino acid compound and hexyldecanol in a continuous aqueous phase; and dispersing a second oil phase in the continuous aqueous phase.

These and other features, aspects, and advantages of the present invention will become evident to those skilled in the art from a reading of the present disclosure.

DETAILED DESCRIPTION OF THE INVENTION

While the specification concludes with the claims particularly pointing and distinctly claiming the invention, it is believed that the present invention will be better understood from the following description.

As used herein, the "cosmetic compositions" are those used to treat or care for, or somehow moisturize, improve, clean the skin, or modify appearance of skin, and include both skin care compositions and color cosmetic compositions. Products contemplated by the phrase "skin care products" comprise, but are not limited to moisturizers, personal cleansing products, occlusive drug delivery patches, nail polish, powders, wipes, hair conditioners, skin treatment emulsions, shaving creams, foundations and the like.

The compositions of the present invention can include, consist essentially of, or consist of, the components of the present invention as well as other ingredients described herein.

The term "keratinous tissue" as used herein, refers to keratin-containing layers disposed as the outermost protective covering of mammals (e.g., humans, dogs, cats, etc.) which includes, but is not limited to, skin, lips, hair, toenails, fingernails, cuticles, hooves, etc.

The term "safe and effective amount" as used herein, refers to an amount of a compound or composition sufficient to significantly induce a positive benefit, preferably a positive keratinous tissue appearance or feel benefit, or positive hair appearance or feel benefit, including independently or in combinations the benefits disclosed herein, but low enough to avoid serious side effects, i.e., to provide a reasonable benefit to risk ratio, within the scope of sound judgment of the skilled artisan.

The term "regulating skin condition" as used herein, refers to improving skin appearance and/or feel, for example, by providing a benefit, such as a smoother appearance and/or feel. The benefit may be a chronic benefit and may include one or more of the following: Reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

All percentages, parts and ratios are based upon the total weight of the compositions of the present invention and all measurements made are at 25° C., unless otherwise designated. All such weights as they pertain to listed ingredients are based on the active level and, therefore, do not include carriers or by-products that may be included in commercially available materials, unless otherwise specified.

The compositions of the present invention are useful for regulating the condition of skin and especially for regulating keratinous tissue condition.

The compositions of the present invention provide additional benefits, including stability, absence of significant (consumer-unacceptable) skin irritation and good aesthetics.

The compositions of the present invention optionally comprise an emulsifier, a skin active, a skin conditioning agent, a sunscreen agent, a thickening agent, and a non-emulsifying crosslinked siloxane elastomer.

The compositions of the present invention optionally comprise additional oil which can solubilize an N-acyl amino acid compound.

The compositions of the present invention are described in detail hereinafter.

N-Acyl Amino Acid Compound

The compositions of the present invention comprise a safe and effective amount of one or more N-acyl amino acid compounds. The amino acid can be one of any of the amino acids known in the art. The N-acyl amino acid compounds of the present invention correspond to the formula:

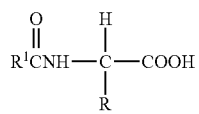

wherein R can be a hydrogen, alkyl (substituted or unsubstituted, branched or straight chain), or a combination of alkyl and aromatic groups. A list of possible side chains of amino acids known in the art are described in Stryer, *Biochemistry*, 1981, published by W.H. Freeman and Company. $R^1$ can be $C_1$ to $C_{30}$, saturated or unsaturated, straight or branched, substituted or unsubstituted alkyls; substituted or unsubstituted aromatic groups; or mixtures thereof.

Preferably, the N-acyl amino acid compound is selected from the group consisting of N-acyl Phenylalanine, N-acyl Tyrosine, their isomers, their salts, derivatives thereof, and mixtures thereof. The amino acid can be the D or L isomer or a mixture thereof. N-acyl Phenylalanine corresponds to the following formula:

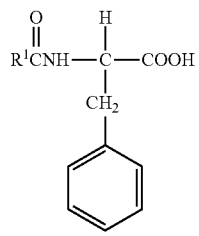

wherein $R^1$ can be $C_1$ to $C_{30}$, saturated or unsaturated, straight or branched, substituted or unsubstituted alkyls; substituted or unsubstituted aromatic groups; or mixtures thereof.

N-acyl Tyrosine corresponds to the following formula:

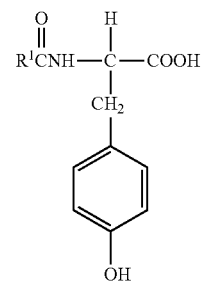

wherein $R^1$ can be $C_1$ to $C_{30}$, saturated or unsaturated, straight or branched, substituted or unsubstituted alkyls; substituted or unsubstituted aromatic groups; or mixtures thereof.

Particularly useful as a topical skin tone evening (lightening or pigmentation reduction) cosmetic agent is N-undecylenoyl-L-phenylalanine. This agent belongs to the broad class of N-acyl Phenylalanine derivatives, with its acyl group being a C11 mono-unsaturated fatty acid moiety and the amino acid being the L-isomer of phenylalanine. N-undecylenoyl-L-phenylalanine corresponds to the following formula:

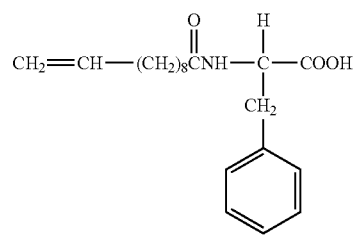

As used herein, N-undecylenoyl-L-phenylalanine is commercially available under the tradename Sepiwhite® from SEPPIC.

The compositions according to the present invention comprise the N-acyl amino acid from about 0.001% to about 10%, preferably from about 0.01 to about 5%, and more preferably from about 0.1% to about 4% by weight of the composition.

Hexyldecanol

The compositions of the present invention comprise hexyldecanol.

The compositions according to the present invention comprise hexyldecanol preferably from about 0.004% to about 50%, more preferably from about 0.04% to about 30%, and more preferably from about 0.4% to about 20% by weight of the composition. The amount of hexyldecanol in the compositions of the present invention can be easily determined upon the amount of an N-acyl amino acid compound and/or the presence of an additional solvent and/or a co-solvent for the N-acyl amino acid compound. Without an additional solvent and a co-solvent, in the compositions of the present invention, the ratio of hexyldecanol to an N-acyl amino acid is preferably no less than 4, and more preferably no less than 5.

Optional Components

Water

The cosmetic compositions of the present invention may comprise water preferably from 10% to 90%, more preferably from about 30% to 80% and more preferably from 40% to 60% by weight of the composition.

Emulsifiers

The composition of the present invention may contain an emulsifier, useful for dispersing and suspending a discontinuous phases in a continuous phase when a product is in an emulsion type. An emulsifier in the present invention can be selected from the group consisting of nonionic emulsifiers, anionic emulsifiers, cationic emulsifiers, amphoteric emulsifiers, and mixtures thereof. When the composition of the present invention contains an emulsifier, in a preferred embodiment, the composition contains from about 0.1% to about 10% emulsifier, more preferably from about 0.2% to about 7.5%, even more preferably from about 0.5% to about 5%, emulsifier by weight of the composition. A wide variety of emulsifying agents can be employed herein.

In one embodiment, non-limiting examples of which include non-ionic and anionic emulsifying agents such as sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, soaps, and mixtures thereof. Nonlimiting examples of other emulsifiers for use herein include: polyethylene glycol 20 sorbitan monolaurate (polysorbate 20), steareth-20, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, polyoxyethylene 20 sorbitan trioleate (polysorbate 85), sorbitan monolaurate, polyoxyethylene 4 lauryl ether sodium stearate, polyglyceryl-4 isostearate, hexyl laurate, PPG-2 methyl glucose ether distearate, ceteth-10, diethanolamine cetyl phosphate, glyceryl stearate, PEG 40 hydrogenated castor oil, PEG-60 hydrogenated castor oil, Glycereth-25 PCA Isostearate, and mixtures thereof.

Another preferred emulsifier herein is cationic emulsifiers. Non-limiting examples of cationic emulsifiers include quaternary ammonium salts or amido-amines having at least one fatty chain containing at least about 8 carbon atoms and mixtures thereof.

Another preferred emulsifier herein is amphoteric emulsifiers. Non-limiting example of amphoteric emulsifiers includes phosphatidylcholine, hydrogenated phosphatidylcholine, lecithin, hydrogenated lecithin, hydroxylated lecithin, lysolecithin and mixtures thereof.

Another preferred emulsifier herein is silicone emulsifiers, including organically modified organopolysiloxanes such as dimethicone copolyols.

Skin Actives

The compositions of the present invention may include at least one skin active compound. Without being bound by theory, it is believed the present compositions provide versatility in formulating a variety of actives.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

Vitamin $B_3$ Compounds

Vitamin $B_3$ compounds such as niacinamide are a preferred skin care active for use herein. The present invention preferably includes from about 0.1% to about 30%, more preferably from about 1% to about 20%, even more preferably from about 2% to about 10% of a vitamin $B_3$ compound.

As used herein, "vitamin $B_3$ compound" means a compound having the formula:

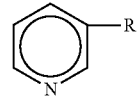

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Whitening Agents

The present compositions may contain a whitening agent. The whitening agent useful herein refers to active ingredients that not only alter the appearance of the skin, but further improve hyperpigmentation as compared to pre-treatment. Useful whitening agents useful herein include ascorbic acid compounds, vitamin $B_3$ compounds, azelaic acid, butyl hydroxy anisole, gallic acid and its derivatives, hydroquinoine, kojic acid, arbutin, mulberry extract, tetrahydrocurcumin, and mixtures thereof. Use of combinations of whitening agents is also believed to be advantageous in that they may provide whitening benefit through different mechanisms.

When used, the compositions preferably contain from about 0.1% to about 10%, more preferably from about 0.2% to about 5%, by weight of the composition, of a whitening agent.

Ascorbic acid compounds are useful whitening agents, and include compounds having the formula (I):

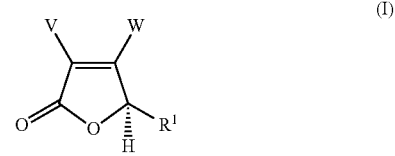

wherein V and W are independently —H or —OH; $R^1$ is —CH(OH)—$CH_2OH$; salts thereof; and derivatives thereof. Preferably, the ascorbic acid compound useful herein is an ascorbic acid salt or derivative thereof, such as the non-toxic alkali metal, alkaline earth metal and ammonium salts commonly known by those skilled in the art including, but not limited to, the sodium, potassium, lithium, calcium, magnesium, barium, ammonium and protamine salts which are prepared by methods well known in the art. Ascorbyl glucoside is a preferably derivative.

Peptides

Peptides, including but not limited to, di-, tri-, tetra-, and pentapeptides and derivatives thereof, may be included in the compositions of the present invention in amounts that are safe and effective. As used herein, "peptides" refers to both the naturally occurring peptides and synthesized peptides. Also useful herein are naturally occurring and commercially available compositions that contain peptides.

When included in the present compositions, peptides are preferably included in amounts of from about $1 \times 10^{-6}$% to about 10%, more preferably from about $1\times10^{-6}$% to about 0.1%, even more preferably from about $1\times10^{-5}$% to about 0.01%, by weight of the composition.

Sugar Amines

The compositions of the present invention may include a safe and effective amount of a sugar amine, which are also known as amino sugars. As used herein, "sugar amine" refers to an amine derivative of a six-carbon sugar. Examples of sugar amines that are useful herein include glucosamine, N-acetyl glucosamine, mannosamine, N-acetyl mannosamine, galactosamine, N-acetyl galactosamine. Preferred for use herein is glucosamine. Additionally, combinations of two or more sugar amines may be used.

When included in the present compositions, a sugar amine is preferably included in amounts of from about 0.001% to about 20%, more preferably from about 1% to about 10%, even more preferably from about 2% to about 5%, by weight of the composition.

Skin Conditioning Agent

Optionally, the composition of the present invention can further comprise a skin conditioning agent. These agents may be selected from humectants, exfoliants or emollients. The amount of skin-condition agent may range from about 1% to about 60%, preferably from about 2% to about 50%, more preferably from about 5% to about 40%, by weight of the composition.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin.

Exfoliants according to the present invention may be selected from C2-C30 alpha-hydroxycarboxylic acids, beta-hydroxycarboxylic acids and salts of these acids. Most preferred are glycolic, lactic and salicylic acids and their ammonium salts.

When the conditioning agent is an emollient it may be selected from hydrocarbons, fatty acids, fatty alcohols and esters.

Sunscreen Agents

The compositions according to the present invention may optionally contain a sunscreen agent selected from an organic sunscreen agent and an inorganic sunscreen agent.

Organic sunscreen agents useful herein include homosalate, octocrylene, octyl-p-methoxycinnamate, phenyl benzimidazole sulfonic acid, 2-hydroxy-4-methoxybenzophenone (Benzophenone-3), 2-ethylhexyl-salicylate, and mixtures thereof.

Inorganic sunscreen agents useful herein include the following metallic oxides; titanium dioxide, zinc oxide, zirconium oxide, iron oxide, and mixtures thereof.

When included in the present compositions, the sunscreens are preferably included in amounts of from about 0.1% to about 20%, preferably from about 0.5% to about 10%, more preferably from about 1% to about 5%, by weight of the composition. Exact amounts will vary depending upon the sunscreen or sunscreens chosen and the desired Sun Protection Factor (SPF).

Thickening Agents

The compositions of the present invention, in some embodiments, may further include one or more thickening agents.

Nonlimiting classes of thickening agents include those selected from the following: carboxylic acid polymers, crosslinked polyacrylate polymers, polyacrylamide polymers, polysaccharides and gums.

When present, the composition preferably includes from about 0.01% to about 5%, more preferably from about 0.1% to about 4%, and still more preferably from about 0.1% to about 3%, by weight of the composition of the thickening agent.

Non-Emulsifying Crosslinked Siloxane Elastomers

The compositions of the present invention may optionally contain non-emulsifying crosslinked siloxane elastomers. The term "non-emulsifying crosslinked siloxane elastomers," as used herein, defines crosslinked organopolysiloxane elastomer from which polyoxyalkylene units or polyglycerin units are absent.

Non-limiting examples of non-emulsifying crosslinked siloxane elastomers used herein include dimethicone/vinyl dimethicone crosspolymers, supplied by a variety of suppliers including Dow Corning™ (DC 9040 and DC 9041), General Electric™ (SFE 839), Shin-Etsu™ (KSG-15, 16, 18 [dimethicone/phenyl vinyl dimethicone crosspolymer]), and Grant Industries (GRANSIL™ line of elastomers). Crosslinked siloxane elastomers useful in the present invention and processes for making them are further described in U.S. Pat. No. 4,970,252 to Sakuta, et al.; U.S. Pat. No. 5,760,116 to Kilgour, et al.; and U.S. Pat. No. 5,654,362 to Schulz, Jr., et al. issued Aug. 5, 1997. Additional crosslinked organopolysiloxane elastomers useful in the present invention are disclosed in Japanese Patent Application JP 61-18708, assigned to Pola Kasei Kogyo KK.

In some embodiments, the composition may contain from about 0.1% to about 15%, preferably from about 0.1% to about 10%, most preferably from about 1% to about 6% of a non-emulsifying crosslinked siloxane elastomer by weight of the composition.

Other Optional Ingredients

A variety of additional ingredients can be incorporated into the compositions of the present invention. Nonlimiting examples of these additional ingredients include; particular materials to modify skin feel or appearance; anti-acne actives; oil-soluble beta-hydroxy acids such as salicylic acid and derivatives thereof; chelators; flavonoid compounds; anti-inflammatory agents; anti-cellulite agents; desquamation actives; anti-oxidant/radical scavengers; tanning actives; skin soothing or skin healing actives such as panthenoic acid derivatives (including panthenol, dexpanthenol, ethyl panthenol), aloe vera, allantoin, bisabolol, and dipotassium glycyrrhizinate; antimicrobial or antifungal actives.

Composition Preparation

The compositions according to the present invention are generally prepared by conventional methods such as are known in the art of making topical compositions. Such methods typically involve mixing of the ingredients in one or more steps to a relatively uniform state, with or without heating, cooling, application of vacuum, and the like.

Products for Topical Use

The topical compositions of the present invention may be formulated into a facial skin cosmetic such as foundations, moisturizer, wrinkle soothing serum, lotion, skin facial mask, skin lotion, skin cream, skin gel, eye gel, eye cream, or any other commonly known skin product or treatment.

In some embodiments, the compositions according to the present invention are in the form of water-in-oil emulsion and comprise an oil phase comprising an N-acyl amino acid compound and hexyldecanol.

In some embodiments, the compositions according to the present invention are in the form of oil-in-water emulsion and comprise an oil phase comprising an N-acyl amino acid compound and hexyldecanol dispersed in a continuous aqueous phase.

In some embodiments, the compositions according to the present invention are in the form of oil-in-water emulsion comprising a first oil phase comprising an N-acyl amino acid compound and hexyldecanol in a continuous aqueous phase, and a second oil phase comprising a non-emulsifying crosslinked siloxane elastomer in the continuous aqueous phase.

Method of Use

Applicants have found that the compositions of the present invention are useful in a variety of applications directed to enhancement of mammalian skin. The methods of use for the compositions disclosed and claimed herein include, but are not limited to: 1) methods of increasing the substantivity of a cosmetic to skin; 2) methods of moisturizing skin; 3) methods of improving the natural appearance of skin; 4) methods of applying a color cosmetic to skin; 5) methods of preventing, retarding, and/or treating wrinkles; 6) methods of providing UV protection to skin; 7) methods of preventing, retarding, and/or controlling the appearance of oil; 8) methods of modifying the feel and texture of skin; 9) methods of providing even skin tone; 10) methods of preventing, retarding, and/or treating the appear of spider vessels and varicose veins; 11) methods of masking the appearance of vellus hair on skin; and 12) methods of concealing blemishes and/or imperfections in human skin, including acne, age spots, freckles, moles, scars, under eye circles, birth marks, post-inflammatory hyperpigmentation, etc. Each of the methods discussed herein involve topical application of the claimed compositions to skin.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Examples 1 and 2

N-undecylenoyl-L-phenylalanine 5 g was added to hexyldecanol 25 g and 40 g, respectively, and the mixtures were heated at about 70-80° C. for 20 min and cooled down to ambient temperature. After that, clarity of the obtained solutions was evaluated visually.

Obtained solutions had clear appearances. No formation of crystals was observed at the time of preparation of the solutions, or after 24 hours at 25° C.

Examples 3-7

Oil-in-water emulsions are prepared by conventional methods from the following components.

TABLE 1

| Components (values in wt %) | Ex. 3 | Ex. 4 | Ex. 5 | Ex. 6 |
|---|---|---|---|---|
| A. Oil phase 1 | | | | |
| Hexyldecanol | 4.0 | 5.0 | 8.0 | 15.0 |
| N-undecylenoyl-L-phenylalanine | 0.4 | 1.0 | 1.0 | 2.5 |
| Isohexadecane | — | — | 1.0 | — |
| B. Oil phase 2 | | | | |
| Dimethicone-6cs*[1] | — | — | 2.0 | — |
| Dow Corning 9040 Silicone Elastomer*[2] | — | — | 4.0 | 2.0 |

TABLE 1-continued

| Components (values in wt %) | Ex. 3 | Ex. 4 | Ex. 5 | Ex. 6 |
|---|---|---|---|---|
| KSG-15*[3] | — | 5.0 | — | — |
| KSG-16*[4] | — | — | — | 3.0 |
| C. Aqueous phase | | | | |
| Carbopol Ultrez 20*[5] | — | 0.3 | 0.3 | 0.5 |
| Polyacrylamide/C13-14 Isoparaffin/Laureth-7*[6] | 1.0 | 0.5 | 0.5 | 1.0 |
| Glycerin | — | 3.0 | 10.0 | 5.0 |
| Phenoxyethanol | 0.2 | 0.2 | 0.2 | 0.2 |
| Niacinamide | 5.0 | 4.0 | 3.0 | 2.0 |
| 1,2-Pentanediol | 3.0 | 3.0 | 2.0 | 3.0 |
| Sodium hydroxide | adjust pH to 6.0-7.0 | | | |
| Water | qs to 100 | | | |

*[1]Dimethicone-6cs: KF-96A-6cs available from Shin-Etsu Chemical Co. Ltd.
*[2]Dow Corning 9040 Silicone Elastomer
*[3]KSG-15: available from Shin-Etsu Chemical Co. Ltd.
*[4]KSG-16: available from Shin-Etsu Chemical Co. Ltd.
*[5]Carbopol Ultrez 20: available from Noveon
*[6]Polyacrylamide/C13-14 Isoparaffin/Laureth-7: Sepigel 305 available from SEPPIC Inc.

Compositions of Examples 3-7 are suitably made as follows:

(1) Phase A: All ingredients are mixed in a vessel using a suitable mixer (e.g., Anchor blade, propeller blade or IKA T25) until the phase become clear under heating at about 70-80° C.

(2) Phase B: All ingredients are mixed in a vessel using a suitable mixer (e.g., Anchor blade, propeller blade or IKA T25) until the phase is homogenous.

(3) Phase C: Disperse polymer powder or polymer thickener premix in water, and neutralize it to target pH if necessary. Add other water soluble ingredients and mix until the phase is homogenous. Solid ingredients, if any, can be pre-dissolved in part of water and then blend into the aqueous phase.

(4) Slowly add Phase A into Phase C and mix until batch is homogenous. For Examples 4-6, slowly add Phase B into the mixture of Phase A and Phase C and mix until batch is homogenous.

Appearance of composition of Example 3 was evaluated visually. No formation of crystals or precipitation was observed at the time of preparation of the composition, or after 5 days at 50° C.

It is understood that the foregoing detailed description of examples and embodiments of the present invention are given merely by way of illustration, and that numerous modifications and variations may become apparent to those skilled in the art without departing from the spirit and scope of the invention; and such apparent modifications and variations are to be included in the scope of the appended claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition for lightening skin tone comprising:
   a) a safe and effective amount of an N-acyl amino acid compound selected from the group consisting of N-acyl amino acid, its isomers, its salts, derivatives thereof, and mixtures thereof, wherein the safe and effective amount of N-acyl amino acid compound provides a skin lightening benefit; and
   b) hexyldecanol, wherein a ratio of hexyldecanol to N-acyl amino acid is no less than 4.

2. The cosmetic composition of claim 1 wherein said N-acyl amino acid is selected from the group consisting of N-acyl phenylalanine, N-acyl tyrosine, their isomers, their salts, derivatives thereof, and mixtures thereof.

3. The cosmetic composition of claim 2 wherein said N-acyl phenylalanine is N-undecylnoyl-L-phenylalanine.

4. The cosmetic composition of claim 1 wherein said composition comprises said N-acyl amino acid compound in the range of from about 0.001% to about 10% by weight of the composition.

5. The cosmetic composition of claim 1 wherein said composition comprises said hexyldecanol in the range of from about 0.004% to about 50% by weight of the composition.

6. The cosmetic composition according to claim 1, wherein said composition further comprises a skin care active selected from the group consisting of vitamin $B_3$ compounds, whitening agents, peptides, sugar amines, and mixtures thereof.

7. The cosmetic composition according to claim 6, wherein said skin care active is vitamin $B_3$ compounds.

8. The cosmetic composition according to claim 1, wherein said composition further comprises sunscreen agents.

9. The cosmetic composition according to claim 1, wherein said composition further comprises an additional solvent for said N-acyl amino acid compound.

10. The cosmetic composition according to claim 1, wherein said composition is oil-in-water emulsion comprising an oil phase comprising said N-acyl amino acid compound and said hexyldecanol dispersed in a continuous aqueous phase.

11. The cosmetic composition according to claim 10, wherein said composition further comprises a non-emulsifying crosslinked siloxane elastomer.

12. A method of regulating the condition of skin, said method comprises applying to the skin of a human, a safe and effective amount of a cosmetic composition according to claim 1.

13. A method of preparing a cosmetic composition for lightening skin tone comprising:
   dispersing a first oil phase comprising a safe and effective amount of an N-acyl amino acid compound and hexyldecanol in a continuous aqueous phase, wherein the safe and effective amount of N-acyl amino acid compound provides a skin lightening benefit; and
   dispersing a second oil phase in the continuous aqueous phase wherein a ratio of hexyldecanol to N-acyl amino acid is no less than 4.

14. The method according to claim 13, wherein said second oil phase comprises a non-emulsifying crosslinked siloxane elastomer.

15. The cosmetic composition of claim 1, further comprising an emulsifier.

* * * * *